US008501740B2

(12) United States Patent
Gutstein

(10) Patent No.: US 8,501,740 B2
(45) Date of Patent: Aug. 6, 2013

(54) METHODS OF TREATMENT OF OPIOID TOLERANCE, PHYSICAL DEPENDENCE, PAIN AND ADDICTION WITH INHIBITORS OF CERTAIN GROWTH FACTOR RECEPTORS

(75) Inventor: Howard Gutstein, Bellaire, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 120 days.

(21) Appl. No.: 12/682,064

(22) PCT Filed: Oct. 8, 2008

(86) PCT No.: PCT/US2008/079198
§ 371 (c)(1),
(2), (4) Date: Apr. 8, 2010

(87) PCT Pub. No.: WO2009/048947
PCT Pub. Date: Apr. 16, 2009

(65) Prior Publication Data
US 2010/0210709 A1    Aug. 19, 2010

Related U.S. Application Data

(60) Provisional application No. 60/978,641, filed on Oct. 9, 2007.

(51) Int. Cl.
| A61K 31/497 | (2006.01) |
| A01N 43/54  | (2006.01) |
| C07D 239/42 | (2006.01) |
| C07D 401/04 | (2006.01) |
| C07D 239/00 | (2006.01) |
| C07D 239/02 | (2006.01) |
| C07D 403/00 | (2006.01) |
| C07D 405/00 | (2006.01) |
| C07D 409/00 | (2006.01) |

(52) U.S. Cl.
USPC ...... 514/252.18; 514/256; 544/242; 544/295; 544/364

(58) Field of Classification Search
USPC ................ 514/252.18, 256; 544/242, 295, 544/364
See application file for complete search history.

(56) References Cited

U.S. PATENT DOCUMENTS

| 6,667,293  | B1  | 12/2003 | Zhao et al.      |        |
| 6,894,051  | B1  | 5/2005  | Zimmermann et al.|        |
| 7,034,013  | B2  | 4/2006  | Thompson et al.  |        |
| 7,115,587  | B2  | 10/2006 | Nerurkar et al.  |        |
| 7,151,106  | B2  | 12/2006 | Hayry            |        |
| 7,544,799  | B2  | 6/2009  | Zimmermann et al.|        |
| 7,629,331  | B2  | 12/2009 | Pipkin et al.    |        |
| 7,635,773  | B2  | 12/2009 | Antle            |        |
| 8,049,003  | B2  | 11/2011 | Mosher et al.    |        |
| 2004/0127453 | A1* | 7/2004  | Lyons et al.    | 514/50 |
| 2005/0043233 | A1 | 2/2005  | Stefanic et al.  |        |
| 2006/0211752 | A1 | 9/2006  | Kohn et al.      |        |

FOREIGN PATENT DOCUMENTS
WO    WO 02/058687 A2 *  8/2002

OTHER PUBLICATIONS

Polakiewicz et al. 1998, "A Mitogen-activated protein kinase pathway is required for u-opioid receptor desensitization." Journal of Biological Chemistry, vol. 273, No. 20, pp. 12402-12406.*
Elliott et al. 1994, "The NMDA receptor antagonists, LY274614 and MK-801, and the nitric oxide synthase inhibitor, NG-nitro-L-arginine . . . " Pain, vol. 56, pp. 69-75.*
Kolesnikov et al. 1993, "Blockade of tolerance to morphine but not to k-opioids by a nitric oxide synthase inhibitor." Proc. Natl. Acad. Sci., vol. 90, pp. 5162-5166.*
Fierro et al. 2007, "Inhibition of platelet-derived growth factor receptorb by imatinib mesylate suppresses proliferation and alters differentiation of human mesenchymal stem cells in vitro." Cell Prolif., vol. 40, pp. 355-366.*
Paniagua et al. 2006, "Selective tyrosine inhibition by imatinib mesylate for the treatment of autoimmune arthritis." The Journal of Clinical Investigation, vol. 116, No. 10, pp. 2633-2642.*
Brewster et al., May 29, 2007, "Cyclodextrins as pharmaceutical solubilizers." Advanced Drug Delivery Reviews, vol. 59, pp. 645-666.*
Beni, Szabolcs, et al., Cyclodextrin/Imatinib Complexation: Binding mode and Charge Dependent Stabilities, Science Direct Nov. 7, 2006.
leCoutre, Phillipp, et al., Pharmacokinetics and Cellular Uptake of Imatinib and its Main Metabolite CGP74588, Cancer Chemother Pharmacol, Dec. 5, 2003.
Peng, Bin, et al., Absolute Bioavailability of Imatinib (Glivec) Orally Versus Intravenous Infusion, Journal of Clinical Pharmacology 44:158-162(2004).
Ahmed, S.H. and G.F. Koob, Transition from Moderate to Excessive Drug Intake: Change in Hedonic Set Point. Science, 1998. 282((5387) Oct. 9): p. 298-300.
Ahmed, S.H., J.R. Walker, and G.F. Koob, Persistent Increase in the Motivation to Take Heroin in Rats With a History of Drug Escalation. Neuropsychopharmacology, 2000. 22: p. 413-421.
Arteaga, C., et. al., A Phase I-II Study of Combined Blockade of the ErbB Receptor Network with Trastuzumab and Gefitinib in Patients with HER2 (ErbB2)-Overexpressing Metastatic Breast Cancer, Clin Cancer Res. Oct. 1, 2008;14(19):6277-83.
Bilsky, E.J., et al., Effects of Naloxone and D-Phe-Cys-Tyr-D-Trp-Arg-Thr-Phe-Thr-NH2 and the Protein Kinase Inhibitors H7 and H8 on Acute Morphine Dependence and Antinociceptive Tolerance in Mice, J. Pharmacol. Exp. Ther., 1996, 277:484-490.
Shen, J., et al., An Antibody Directed Against PDGF Receptor b Enhances the Antitumor and the Anti-Angiogenic Activities of an Anti-VEGF Receptor 2 Antibody Biochem Biophys Res Commun. Jun. 15, 2007; 357(4):1142-7. Epub Apr. 19, 2007.

(Continued)

*Primary Examiner* — Kara R McMillian
(74) *Attorney, Agent, or Firm* — Parker Highlander PLLC

(57) ABSTRACT

Methods of preventing the development and reversing or partially reversing opioid tolerance in a subject are provided herein. Such methods include the step of administering to a subject in need thereof a therapeutically effective amount of a PDGFR modulator or EGFR modulator alone or together with an opiate analgesic. The methods can also be used for the treatment of refractory neuropathic pain, physical dependence or addiction.

5 Claims, 9 Drawing Sheets

OTHER PUBLICATIONS

Chen, L., et al., Protein Kinase C Reduces Mg2+ Block of NMDA-Receptor Channels as a Mechanism of Modulation, Nature, 1992, 356:521-523.
Chen, L., et al., Sustained Potentiation of NMDA Receptor-Mediated Glutamate Responses Through Activation of Protein Kinase C by a μ-Opioid, Neuron, 1991, 7:319-326.
Chung, J.M., H.K. Kim, and K. Chung, Segmental spinal nerve ligation model of neuropathic pain. Methods Mol Med, 2004. 99: p. 35-45.
Druker, B.J., et al., Efficacy and Safety of a Specific Inhibitor of the BCR-ABL Tyrosine Kinase in Chronic Myeloid Leukemia, N. Engl. J. Med., 2001, 344:1031-1037.
Elliott, K., et al., The NMDA Receptor Antagonists, LY274614 and MK-801, and the Nitric Oxide Synthase Inhibitor, NG-Nitro-L-Arginine, Attenuate Analgesic Tolerance to the Mu-Opioid Morphine but not to Kappa Opioids, Pain, 1994,56:69-75.
Foley, K.M., et al., Opioids and Chronic Neuropathic Pain, NEJM, 2003, 348:1279-1281.
Gutstein and Akil, Opioid Analgesics,Pharmacological Basis of Therapeutics, 11th edition 2006, 547-590.
Gutstein and Trujillo, Does Chronic Nociceptive Stimulation Alter the Development of Morphine Tolerance? Brain Research 1995, 680, 173-179.
Gutstein et al., MK-801 Inhibits the Development of Morphine Tolerance at Spinal Sites, Brain Research1993, 626, 332-334.
Gutstein,H.B. The Effects of Pain on Opioid Tolerance: How Do We Resolve the Controversy? Pharmacological Reviews 1996, 48:3, 403-407.
Jordan, B.A., et al., G-protein-Coupled Receptor Heterodimerization Modulates Receptor Function, Nature, 1999, 399:697-700.
Kieffer, B.L., et al., Opioids: First Lessons from Knockout Mice, Trends Pharmacol Sci., 1999, 20: 19-26.
Kolesnikov, Y.A., et al., Blockade of Tolerance to Morphine but not to Opioids by a Nitric Oxide Synthase Inhibitor, Proc Natl Acad Sci USA, 1993, 90:5162-516.
Kotecha, S.A., et al., A D2 class dopamine receptor transactivates a receptor tyrosine kinase to inhibit NMDA receptor transmission. Neuron, 2002. 35(6): p. 1111-22.
20. Kumar A, et. al., Structure and Clinical Relevance of the Epidermal Growth Factor Receptor in Human Cancer, J Clin Oncol. Apr. 1, 2008;26(10):1742-51.
Lev, D.C., et al., Inhibition of Platelet-Derived Growth Factor Receptor Signaling Restricts the Growth of Human Breast Cancer in the Bone of Nude Mice, J. Cancer Res., 2005, 11(1):306-14.
Mao, J., et al., Chronic Morphine Induces Down Regulation of Spinal Glutamate Transporters: Implications in Morphine Tolerance and Abnormal Pain Sensitivity, J. Neuroscience, 2002, 22(18):8312-8323.
Mao, J., et al., Mechanisms of Hyperalgesia and Opiate Tolerance: a Current View of Their Possible Interactions, Pain, 1995, 62:259-274.
Mao, J., et al., Thermal Hyperalgesia in Association with the Development of Morphine Tolerance in Rats: Roles of Excitatory Amino Acid Receptors and Protein Kinase C, J. Neurosci., 1994, 14:2301-2312.
McGary, E.C., et al., Inhibition of Platelet-Derived Growth Factor-Mediated Proliferation of Osteosarcoma Cells by the Novel Tyrosine Kinase Inhibitor STI571, Clinical Cancer Res., 2002, 8(11):3584-91.
Mori, S., et al., Identification of Two Juxtamembrane Autophosphorylation Sites in the PDGF Beta-Receptor; Involvement in the Interaction with Src Family Tyrosine Kinases, EMBO J., 1993, (6):2257-64.
Ossipov, M.H., et al., The Loss of Antinociceptive Efficacy of Spinal Morphine in Rats With Nerve Ligation Injury Is Prevented by Reducing Spinal Afferent Drive, Neurosci Lett., 1995, 199:87-90.
Paez JG, et. al., EGFR Mutations in Lung Cancer: Correlation With Clinical Response to Gefitinib Therapy, Science 2004; 304(5676): 1497-500.
Pasternak, G.W., et al., Mapping of Opioid Receptors Using Antisense Oligodeoxynucleotides: Correlating their Molecular Biology and Pharmacology, 1995, Trends in Pharmacol. Science, 1995, 16:344-350.
Sjogren, P., et al., Hyperalgesia and Myoclonus in Terminal Cancer Patients Treated With Continuous Intravenous Morphine, Pain, 1993, 55:93-97.
Stewart D, et. al., Gefitinib Maintenance in Stage III Non-Small-Cell Lung Cancer, Clin Oncol. Sep. 8, 2008.
Trang, T., et al., The Role of Spinal Neuropeptides and Prostaglandins in Opioid Physical Dependence, Br. J. Pharmacol., 2002, 136(1):37-48.
Wang, H.Y., M. Frankfurt, and L.H. Burns, High-Affinity Naloxone Binding to Filamin A Prevents Mu Opioid Receptor-Gs Coupling Underlying Opioid Tolerance and Dependence, PLoS ONE, 2008.
Yan L, et. al., Pharmacogenetics and Pharmacogenomics in Oncology Therapeutic Antibody Development, BioTechniques 2005; 39(4): 565-8.
Belcheva, MM., et al., The Fibro Growth Factor Is at the Site of Convergence between u-Opioid Receptor and Growth Factor Signaling Pathways in Rat C6 Glioma Cells, JPET, 2002, 303:3, 909-918.
Li, J, et al., Mechanism of Agonist-Induced Down-Regulation of the Human k-Opioid Receptor: Internalization Is Required for Down-Regulation, M.Pharm, 2000, 58:4, 795-801.
Dong et al.,"Selective inhibition of PDGFR by imatinib elicits the sustained activation of ERK and downstream receptor signaling in malignant glioma cells," *International Journal of Oncology*, 38:555-569, 2011.
Chu et al., "BCR/ABL kinase inhibition by imatinib mesylate enhances MAP kinase activity in chronic myelogenous leukemia CD34+ cells," *Blood*, 103(8):3167-3174, 2004.
Johnson et al., "Induction of heparin-binding EGF-like growth factor and activation of EGF receptor in imatinib mesylate-treated squamous carcinoma cells," *Journal of Cellular Physiology*, 205:218-227, 2005.
Karaman et al., "A quantitative analysis of kinase inhibitor selectivity," *Nature Biotechnology*, 26(1):127-132, 2008, and Supplemental Materials.
Mouléedous et al., "Extracellular signal-regulated kinase (ERK) inhibition does not prevent the development or expression of tolerance to and dependence on morphine in the mouse," *Pharmacology, Biochemistry and Behavior*, 88:39-46, 2007.
Servidei et al., "Increased sensitivity to the platelet-derived growth factor (PDGF) receptor inhibitor STI571 in chemoresistant glioma cells is associated with enhanced PDGF-BB-mediated signaling and STI571-induced Akt inactivation," *Journal of Cellular Physiology*, 208:220-228, 2006.
Yu et al., "Pharmacologic mitogen-activated protein/extracellular signal-regulated kinase kinase/mitogen-activated protein kinase inhibitors interact synergistically with STI571 to induce apoptosis in Bcr/Abl-expressing human leukemia cells," *Cancer Research*, 62:188-199, 2002.

* cited by examiner

METHODS OF TREATMENT OF OPIOID TOLERANCE, PHYSICAL DEPENDENCE, PAIN AND ADDICTION WITH INHIBITORS OF CERTAIN GROWTH FACTOR RECEPTORS

CROSS-REFERENCE TO RELATED APPLICATIONS

This application claims priority to U.S. Pat. App. Ser. No. 60/978,641 filed Oct. 9, 2007. The application is incorporated by reference herein in its entirety.

STATEMENT REGARDING FEDERALLY SPONSORED RESEARCH OR DEVELOPMENT

This invention was made with government support under Grant No. DA15146 awarded by the National Institutes of Health. The government has certain rights in the invention.

THE NAMES OF THE PARTIES TO A JOINT RESEARCH AGREEMENT

None.

REFERENCE TO SEQUENCE LISTING

None.

BACKGROUND

Opioids are analgesic agents which exhibit opium or morphine-like properties. Both acute and chronic opioid administration can produce tolerance, as indicated by a lowered responsiveness to the administration of this drug. Drug tolerance necessitates higher doses, which can be associated with side effects that often limit long-term use. Mao, J., et al., *Chronic Morphine Induces Down Regulation of Spinal Glutamate Transporters: Implications in Morphine Tolerance and Abnormal Pain Sensitivity*, J. Neuroscience, 2002, 22(18):8312-8323; Sjogren, P., et al., *Hyperalgesia And Myoclonus In Terminal Cancer Patients Treated With Continuous Intravenous Morphine*, Pain, 1993, 55:93-97; Ossipov, M. H., et al., *The Loss of Antinociceptive Efficacy of Spinal Morphine In Rats With Nerve Ligation Injury Is Prevented By Reducing Spinal Afferent Drive*, Neurosci Lett., 1995, 199: 87-90; Foley, K. M., et al., Opioids and Chronic Neuropathic Pain, NEJM, 2003, 348:1279-1281.

Tolerance to the analgesic effects of narcotics remains a major impediment to the use of these drugs in the treatment of pain Also, pain due to nerve compression or nerve invasion is a prominent component of cancer pain, and is resistant to treatment with currently available narcotic and non-narcotic analgesics.

Current methods of treating opioid tolerance often involve the NMDA receptor and inhibiting it. NMDA antagonists, however, have been found to be highly toxic and are only able to partially reverse morphine tolerance at best and cannot reverse established tolerance. The high toxicity limits the clinical use of antagonists. Hence, a need exists for compositions and methods for: (1) the effective inhibition of the development of opioid tolerance; (2) reversal or reduction of opioid tolerance; (3) reducing opioid dependence; (4) effective inhibition of physical dependence; and (5) reducing or inhibition of addiction.

SUMMARY OF THE INVENTION

Methods of modulating Platelet Derived Growth Factor Receptor ("PDGFR") and/or Epidermal Growth Factor Receptor ("EGFR") for the treatment of opioid tolerance, physical dependence, chronic pain, addiction and related disorders are provided herein. As described herein, methods of preventing, reducing and/or reversing opioid tolerance by administering to a patient in need thereof a therapeutically effective amount of a PDGFR or EGFR small molecule inhibitor formulated in a vehicle permitting the drug to cross the blood-brain barrier, alone or in combination, and/or in combination with morphine or another opiate analgesic drug or narcotic are provided. As such, these combination therapies can be further facilitated by a formulation of the drug product(s) with cyclodextrin and cyclodextrin derivatives.

Furthermore, many types of compounds which possess PDGFR inhibiting activity or EGFR inhibiting activity can be useful in the treatment of opioid tolerance, physical dependence, pain, addiction and related disorders Therefore, as described herein, methods of treatment are provided wherein the method comprises the step of administering to a patient in need thereof a therapeutically effective amount of a PDGFR or EGFR inhibitor and administered, alone, or in combination with morphine or another opiate analgesic drugs or narcotics.

BRIEF DESCRIPTION OF THE DRAWINGS

The foregoing and other features and aspects of the present disclosure will be best understood with reference to the following detailed description of a specific embodiment of the disclosure, when read in conjunction with the accompanying drawings, wherein.

DETAILED DESCRIPTION OF THE INVENTION

Figure 1:
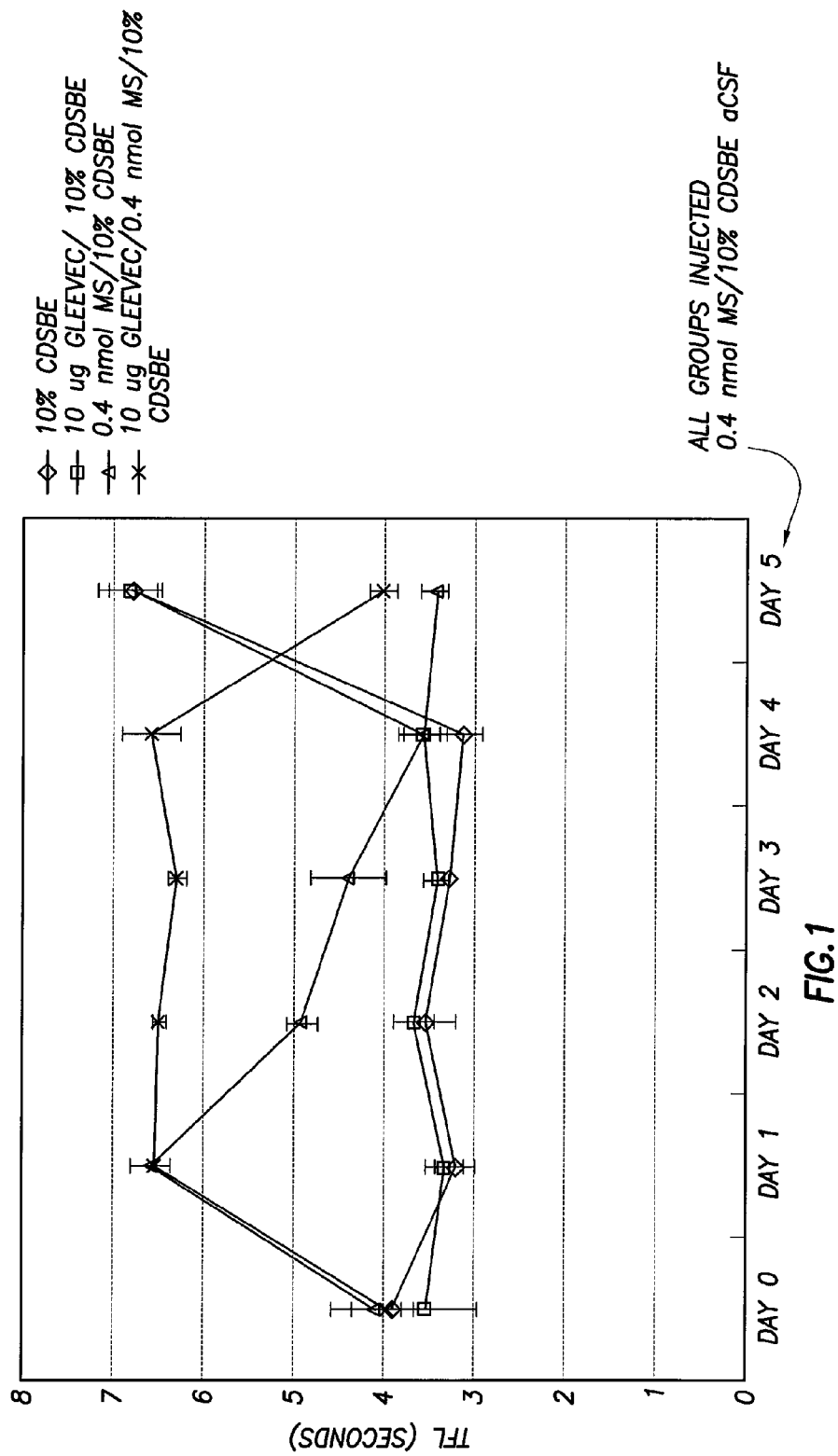
FIG. 1 shows the effectiveness of administering GLEEVEC® (imatinib) in 10% CAPTISOL® (sulfobutylether-β-cyclodextrin) (also known as CDSBE) in the tail flick latency test, along with controls demonstrating that GLEEVEC® (imatinib) and CDSBE do not exhibit analgesic effects, or interfere with the analgesic effects of morphine administered after chronic GLEEVEC® (imatinib) or CDSBE alone.

A correlation between pain response in animals treated with opioids and the inhibition of the PDGFR and/or EGFR has been shown. Specifically, opioids are often used for pain management. Prolonged administration of opiates is associated with significant problems including the development of antinociceptive tolerance, where higher doses are required to manage the pain. Higher doses of opioids result in serious toxic effects including nausea, dizziness, constipation, impairment of mental alertness and physical dependence. Opioid use also introduces the risk of developing drug addiction. These side effects do not develop tolerance at the same rate as analgesia and can become dose-limiting in patients on extremely high doses of opioids.

Opiods include any natural or synthetic opioid analgesic, such as, for example, morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levo-alphacetylmethadol (LAAM), loperamide (used for diarrhea, does not cross the blood-brain barrier), diphenoxylate (used for diarrhea, does not appreciably cross the blood-brain barrier), pentazocine, phenazocine, buprenorphine, etorphine, butorphanol, nalbuphine, levorphanol, levomethorphan, dezocine, lefetamine, tilidine, and tramadol, propoxyphene, or oxycodone. An opioid also encompasses any natural or synthetic narcotic antagonist such as nalmefene, naloxone or naltrexone as well as any natural or synthetic mixed opioid agonist/antagonist such as nalbuphine, butorphanol, buprenorphine or pentazocine; or any pharmaceutically acceptable composition thereof.

Opioids mediate their potent analgesic effects via interaction with specific receptors present on neurons in the brain, spinal cord and periphery. These receptors belong to the 7 transmembrane G-protein coupled receptor (GPCR) family. Kieffer, B. L., et al., *Opioids: First Lessons from Knockout Mice*, Trends Pharmacol Sci., 1999, 20: 19-26. Three distinct type of receptors, namely mu, delta and kappa have been identified. These receptors are targeted by endogenous opioid peptides and by selective agonistic or antagonistic ligands. Endomorphins target mu receptors; enkephalins target delta receptors; and dynorphins target kappa receptors. Other opioid receptor subtypes designated as mu.sub.1 and mu.sub.2, delta.sub.1 and delta.sub.2, and kappa.sub.1, kappa.sub.2, kappa.sub.3 and kappa.sub.4 have also been identified. Pasternak, G. W., et al., *Mapping of Opioid Receptors Using Antisense Oligodeoxynucleotides: Correlating their Molecular Biology and Pharmacology*, 1995, Trends in Pharmacol. Science, 1995, 16:344-350.

The basis for the additional receptor heterogeneity is unclear but is attributed to alternate processing of gene products and/or receptor oligomerization. Jordan, B. A., et al., *G-protein-Coupled Receptor Heterodimerization Modulates Receptor Function*, Nature, 1999, 399:697-700.

Opoid tolerance can be classified as a group of homeostatic changes in specific neural circuitry that decreases analgesic efficacy and leads to physical dependence upon opioids. Multiple factors contribute to the development of tolerance. Trang, T., et al., *The Role of Spinal Neuropeptides and Prostaglandins in Opioid Physical Dependence*, Br. J. Pharmacol., 2002, 136(1):37-48. Tolerance may develop as a result of paradoxical stimulatory actions of opioids exerted at very low doses that progressively overwhelm the inhibitory effects contributing to analgesia. Wang, H. Y., M. Frankfurt, and L. H. Burns, *High-Affinity Naloxone Binding To Filamin A Prevents Mu Opioid Receptor-Gs Coupling Underlying Opioid Tolerance And Dependence*, PLoS ONE, 2008. 3(2): 1554 To date, several CNS regions have been identified as important mediators of tolerance and physical dependence, such as the nucleus accumbens (NAcc), ventral tegmental area (VTA), arcuate nucleus (Arc), amygdala (Amy), periaqueductal grey (PAG), locus coeruleus (LC), rostral ventromedial medulla (RVM), and nucleus tractus solitarius (NTS), as well as the spinal cord. See e.g., Gutstein et al., 1993. At the cellular level, opioid receptor function is altered.

For example, with chronic administration of an opioid, some cellular pathways undergo adaptive changes that appear to oppose the acute effects of opioids. These changes are held in check by continued opioid administration, but unmasked when opioids are withdrawn, leading to hyperexcitability and increased signaling in affected systems. These changes may underlie the clinical withdrawal syndrome. Notwithstanding, despite the similarities in signal transduction mechanisms, the effects caused by the opioid receptor subtypes are different. For example, mu and delta opioid agonists can produce euphoria and are positive reinforcers, whereas kappa agonists cause dysphoria and are negative reinforcers. Gutstein and Akil, *Pharmacological Basis of Therapeutics*, $11^{th}$ edition 2006. To date, whether these properties can be completely explained by anatomic differences in the localization of different opioid receptor types is unclear and suggests that other signal transduction mechanisms may be involved in mediating opioid effects.

Activation of N-methyl-D-aspartate receptors and protein kinase C, $G\beta\gamma$ subunits, NO/cGMP, calcium/calmodulin kinase pathways as well as regulation of glutamate transporters have been implicated in the mechanisms of opioid tolerance, suggesting a possible link between neural plasticity and the mechanisms of opioid tolerance. Opioid receptors generally couple to $G_1$ and $G_o$ classes of G proteins and acutely inhibit cyclic adenosine monophosphate formation, inhibit calcium conductance, and activate a potassium conductance, leading to cell hyperpolarization. Childers, S., *Opioid Receptor-Coupled Second Messenger Systems, Handbook of Experimental Pharmacology: Opioids I*. Edited by A. Herz. Berlin, Springer, 1993, pp 189-216.

Opioids may also activate protein kinase C (PKC). PKC activates the NMDA receptor, a known mediator of tolerance and dependence. Chen, L., et al., *Sustained Potentiation of NMDA Receptor-Mediated Glutamate Responses Through Activation of Protein Kinase C by a μ-Opioid*, Neuron, 1991, 7:319-326; Mao, J. et al., *Increases in Protein Kinase C Gamma Immunoreactivity in the Spinal Cord of Rats Associated with Tolerance to the Analgesic Effects of Morphine*, Brain Res., 1995, 677:257-267.

PKC may directly or indirectly modulate NMDARs by removing the $Mg^{++}$ blockade from the NMDAR-$Ca^{2+}$ channel site and regulating NMDAR trafficking and gating. Chen, L., et al., *Protein Kinase C Reduces $Mg^{2+}$ Block of NMDA-Receptor Channels as a Mechanism of Modulation*, Nature, 1992, 356:521-523 and Xiong, Z. G., et al., *Regulation of*

*N-Methyl-D-Aspartate Receptor Function by Constitutively Active Protein Kinase C*, Mol. Pharmacol., 1998, 54:1055-1063.

Chronic morphine use also induced spinal glutamate transporter downregulation that was preventable by the NMDAR inhibition. Decreased levels of spinal GTs result in reduced ability to maintain glutamate homeostasis, thereby increasing the availability of extracellular glutamate. Increased glutamate availability at the extracellular level increases the probability of excitatory amino acid receptor activation including NMDARs. Conceivably, activation of NMDARs under such circumstances could make contributions to the previously proposed intracellular mechanisms of morphine tolerance that involve PKC, cAMP, and nitric oxide Kolesnikov, Y. A., et al., *Blockade of Tolerance to Morphine but not to Opoids by a Nitric Oxide Synthase Inhibitor*, Proc Natl Acad Sci USA, 1993, 90:5162-516; Elliott, K., et al., *The NMDA Receptor Antagonists, LY274614 and MK-801, and the Nitric Oxide Synthase Inhibitor, NG-Nitro-L-Arginine, Attenuate Analgesic Tolerance to the Mu-Opioid Morphine but not to Kappa Opioids*, Pain, 1994, 56:69-75; Mao, J. et al., *Increases in Protein Kinase C Gamma Immunoreactivity in the Spinal Cord of Rats Associated with Tolerance to the Analgesic Effects of Morphine*, Brain Res., 1995, 677:257-267.

Opioids mediate their potent analgesic effects via interaction with specific receptors, belonging to the G-protein coupled receptor (GPCR) family, present on cells in the brain, spinal cord and periphery. Three distinct type of receptors, namely mu, delta and kappa have been identified. Activation of N-methyl-D-aspartate receptors and protein kinase C, desensitization of the g-protein coupled receptors, as well as regulation of glutamate transporters have been implicated in the mechanisms of opioid tolerance. Mao, J., et al., *Thermal Hyperalgesia in Association with the Development of Morphine Tolerance in Rats: Roles of Excitatory Amino Acid Receptors and Protein Kinase C*, J. Neurosci., 1994, 14:2301-2312; Mao, J., et al., *Mechanisms of Hyperalgesia and Opiate Tolerance: a Current View of Their Possible Interactions*, Pain, 1995, 62:259-274. Furthermore, there has been some teaching as to the possible role of downregulation or receptor internalization in the development of opioid tolerance. Cox, B. M., *Molecular and Cellular Mechanisms in Opioid Tolerance, Towards a New Pharmacotherapy of Pain*, A. I. Basbaum and J. M. Besson, Editors. 1991, John Wiley & Sons. p. 137-156

Co-administration of NMDA antagonists have been found to be effective in reducing the tolerance to opioid analgesics seen with chronic administration in animal models of pain. Bilsky, E. J., et al., *Effects of Naloxone and D-Phe-Cys-Tyr-D-Trp-Arg-Thr-Phe-Thr-NH2 and the Protein Kinase Inhibitors H7 and H8 on Acute Morphine Dependence and Antinociceptive Tolerance in Mice*, J. Pharmacol. Exp. Ther., 1996, 277:484-490. However, these can only partially reverse tolerance at best, and cannot reverse established opioid tolerance. Besides, NMDA antagonists are highly toxic, which severely limits their clinical use.

Methods of inhibiting the development of opioid tolerance, and/or reverse or partially reverse tolerance, and/or reduce dependency of an opioid by specifically inhibiting PDGFR or EGFR are provided. These methods are also useful to treat disorders sometimes associated with opioid tolerance such as pain. Such methods comprise administrating to a subject in need thereof a therepeutically effective amount of PDGFR or EGFR modulator alone, and/or in combination with the administration of morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levo-alphacetylmethadol (LAAM), loperamide (used for diarrhea, does not cross the blood-brain barrier), diphenoxylate (used for diarrhea, does not appreciably cross the blood-brain barrier), pentazocine, phenazocine, buprenorphine, etorphine, butorphanol, nalbuphine, levorphanol, levomethorphan, dezocine, lefetamine, tilidine, and tramadol.

Opioid tolerance may occur in any subject experiencing chronic pain associated with disease including, for example, cancer, multiple sclerosis, HIV-associated neuropathy, diabetic neuropathy, trigeminal neuralgia, post herpetic neuralgia (shingles), phantom limb pain, nerve injury due to trauma or surgery, and deafferentation pain, where the subject is or has been previously been administered an opioid. Gutstein, Pharmacological Reviews 1996. Pain may increase the analgesic requirement but does not typically affect opioid tolerance per se. Gutstein and Trujillo, Brain Research 1995.

EGFR is cell surface receptor expressed in most tissue. EGFR transitions from a monomeric form to an active homodimer. This dimerization stimulates the autophosphorylation of C-terminal tyrosine residues and activates the receptor. In addition to dimerization, EGFR might become active when paired with other members of the ErbB receptor family. Proper expression of EGFR promotes cell growth and proliferation, while aberrant over expression of the receptor leads to several cancers such as lung cancer. See e.g., Kumar A, et. al., *Structure and Clinical Relevance Of The Epidermal Growth Factor Receptor In Human Cancer*, J Clin Oncol. 2008 Apr. 1; 26(10):1742-51.

As used herein, modulators can be inhibitors (antagonists) or agonists. Specifically, EGFR inhibitors include small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib, and most recently, lapatinib. See e.g., Yan L, et. al., *Pharmacogenetics and Pharmacogenomics In Oncology Therapeutic Antibody Development*, BioTechniques 2005; 39(4): 565-8, and Paez J G, et. al., *EGFR Mutations In Lung Cancer Correlation With Clinical Response To Gefitinib Therapy*, Science 2004; 304 (5676): 1497-500.

As to small molecule EGFR inhibitors, gefitinib, marketed as IRESSA® (gefitinib), is a selective inhibitor of EGFR that operates by blocking the kinase domain of the receptor, preventing it from acquiring ATP, which results in the inability of the receptor to activate downstream targets. It has been successful in treating lung cancer but has not extensively been studied as a treatment for other forms of cancer. See, Arteaga C, et. al., *A Phase I-II Study of Combined Blockade of the ErbB Receptor Network with Trastuzumab and Gefitinib in Patients with HER2 (ErbB2)-Overexpressing Metastatic Breast Cancer*, Clin Cancer Res. 2008 Oct. 1; 14(19):6277-83. Gefitinib specifically targets the kinase domain of EGFR, blocking the ability of the receptor to function and active downstream targets. This mode of activity has been demonstrated to successfully block the progression of local malignancies in lung cancer. See, Stewart D, et. al., *Gefitinib Maintenance in Stage III Non-Small-Cell Lung Cancer*, Clin Oncol. 2008 Sep. 8. Other small molecule EGFR inhibitors include lapatinib (TykerB) and erlotinib (Tarceva). EGFR is highly expressed in the central nervous system and is known to be involved in the development, survival, growth, and differentiation of neurons and glial cells.

Likewise, PDGFRs are expressed in virtually every region of the central nervous system where they are involved in the development, survival, growth, and differentiation of both neuronal and glial cells, and is enriched in the pain-processing regions of the spinal cord. PDGFRs are tyrosine kinase-coupled receptors that dimerize upon ligand activation and become autophosphorylated on tyrosine residues. These residues act as binding sites for a group of proteins that contain Src homology 2 (SH2) domains. Phospholipase C-γ, the protein-tyrosine phosphatase Syp (PTP-Syp), Ras GTPase-activating protein (Ras-GAP), the Src family of protein-tyrosine kinases, phosphatidylinositol 3-kinase (PI3K), and several adaptor-type signal transduction proteins (Shc, Grb2, Shb, and Nck) all bind to activated PDGFR-α and PDGFR-β via SH2 domains. See e.g., Mori, S., et al., *Identification of Two Juxtamembrane Autophosphorylation Sites in the PDGF Beta-Receptor; Involvement in the Interaction with Src Family Tyrosine Kinases*, EMBO J., 1993, (6):2257-64.

PDGFR modulators useful in connection with the methods of treatment provided herein include small molecule antagonists, antibodies, specific antisense nucleotide or siRNA. For example the modulator may be an aptamer inhibitor as described in U.S. Pat. Nos. 6,699,843 and 7,141,375. In particular, the inhibitor may include small molecule inhibitors such as imatinib mesylate (GLEEVEC® (imatinib), STI571), sunitinib, sorafenib, Tyrphostin AG 1296, axitinib (AG-013736), 6,7-(dimethoxy-2,4-dihydroindeno[1,2-c]pyrazol-3-yl)-β-fluoro-phenyl)-amine. Other examples of small molecule inhibitors may include, for example, those found in U.S. Pat. Nos. 5,238,950, 5,646,285, 5,891,737, 6,974,816, and 7,087,608 and those found in published U.S. Application No. 20040132754. Other inhibitors that have been developed include ABT-869 (Abbott Laboratories, Chicago, Ill.), AEE788 (Novartis, Cambridge, Mass.), and AMG 706 (Amgen, Thousand Oaks, Calif.). More specifically, drugs that can modulate PDGFR-beta are useful in connection with the methods taught herein, such as PDGFR13 mAB by Imclone. See e.g., Biochem Biophys Res Commun. 2007 Jun. 15; 357(4):1142-7. Epub 2007 Apr. 19.

GLEEVEC® (Imatinib), a 2-phenylaminopyrimidine derivative, is particularly useful in methods of treating opioid tolerance. Imatinib occupies the Tyrosine Kinase active site, leading to a decrease in activity. It was initially developed as a small-molecule protein tyrosine kinase inhibitor, to target the gene product of the Philadelphia chromosome Bcr/Abl translocation in chronic myelogenous leukemia (CML). Imatinib was initially approved by the US and European regulatory agencies for the treatment of Bcr/Abl-positive CML. Druker, B. J., et al., *Efficacy and Safety of a Specific Inhibitor of the BCR-ABL Tyrosine Kinase in Chronic Myeloid Leukemia*, N. Engl. J. Med., 2001, 344:1031-1037.

Imatinib has been demonstrated to inhibit the receptor tyrosine kinase activity of the PDGF receptor. Lev, D. C., et al., *Inhibition of Platelet-Derived Growth Factor Receptor Signaling Restricts the Growth of Human Breast Cancer in the Bone of Nude Mice*, J. Cancer Res., 2005, 11(1):306-14; McGary, E. C., et al., *Inhibition of Platelet-Derived Growth Factor-Mediated Proliferation of Osteosarcoma Cells by the Novel Tyrosine Kinase Inhibitor STI571*, Clinical Cancer Res., 2002, 8(11):3584-91. Imatinib may be delivered spinally or systematically with about 10% CDSBE (cyclodextrin sulfobutyl ether).

The modulators of PDGFR and EGFR are useful in connection with the methods described herein may be administered to the subject spinally, and by other modes of administration. For example, the modulator (inhibitor or agonist) may be introduced intravenously, intraperitoneally, intramuscularly, subcutaneously or orally administered. Additionally, it may be administered to the subject via a catheter. For effective administration, the modulator crosses the blood brain barrier. To achieve this, modulators may be modified in structure or vehicle to allow crossing of the blood brain barrier. To achieve this, the modulator must be solubilized in an aqueous solution. This is because organic solvents normally used to solubilize hydrophobic compounds such as EGFR and PDGFR inhibitors have severe neurotoxic effects upon the spinal cord and other tissues of the nervous system. Also, organic solvents cause extreme pain and tissue damage when injected subcutaneously, intramuscularly, or intravenously. Organic solvents can also cause systemic organ damage and even death. Cyclodextrins are known to block the P-glycoprotein transporter that removes many compounds from the brain to the circulation. Thus, drugs that initially cross the blood-brain barrier are retained in the brain and spinal cord.

The modulators of EGFR and PDGFR used in connection with the methods described herein may be administered to the subject spinally, and by other modes of administration. For example, the modulator/inhibitor may be introduced intravenously, intraperitoneally, intramuscularly, subcutaneously, or orally administered. Additionally, it may be administered to the subject via a catheter. For effective administration, the modulator crosses the blood brain barrier. To achieve this, modulators may be modified in structure to allow crossing of the blood brain barrier.

Hence, the modulator may be formulated with special drug delivery vehicles such as, for example, liposomes, cyclodextrins, cyclodextrans, or other cycloamyloses, biocompatible and/or degradable polymers, and the like. For example, GLEEVEC® (imatinib), also referred to herein as Imatinib (2-phenylaminopyrimidine derivative), can be solubilized in cyclodextrin. For intrathecal injection, GLEEVEC® (imatinib)/IRESSA® (gefitinib) are dissolved in 20 μA of a solution of artificial cerebrospinal fluid (aCSF 126 mM of NaCL, 2.5 mM of KCl, 1.2 mM of $NaH_2PO_4$, 1.2 mM of $MgCl_2$, 2.4 mM of $CaCl_2$, 11 mM of glucose, and 25 mM of $NaHCO_3$, saturated with 5% $CO_2$ in 95% $O_2$, and adjusted to a pH value of 7.3-7.4) and 10% final concentration (w/v) sulfobutylether-7-b-cyclodextrin (CAPTISOL® (sulfobutylether-β-cyclodextrin), Cydex, Lenexa, Kans.). For subcutaneous administration, morphine sulfate and GLEEVEC® (imatinib)/IRESSA0 (gefitinib) are dissolved in a solution of normal saline containing 10% CAPTISOL® (sulfobutylether-β-cyclodextrin).

For example, to treat opioid tolerance and the other indications described herein, the opioid and the PDGFR modulator, or the opioid and the EGFR modulator, may be administered separately or in combination with the opioid to the subject in need thereof and either at the same time or at different intervals. Specifically, the opioid and the PDGFR modulator, or the EGFR modulator, can be combined in a single formulation.

Further disclosed herein is a method for inhibiting the development of opioid tolerance in a subject including administering to the subject therapeutically effective amounts of a PDGFR or EGFR small molecule modulator, wherein the inhibitor is present in a pharmaceutically acceptable formulation. This formulation can contain cyclodextrin together with a preservative, antioxidant, buffering agent, acidifying agent, alkalizing agent, antibacterial agent, antifungal agent, solubility enhancing agent, complexation enhancing agent, solvent electrolyte, salt, water, stabilizer, tonicity modifier, antifoaming agent, oil, emulsifying agent, bulking agent, cryoprotecant or a combination thereof. For definitions and more examples, see U.S. Pat. No. 7,034,013, beginning at Column 20, line 17 through Column 23, line 25, incorporated herein by reference.

As described in U.S. Pat. No. 7,034,013, an injectable formulation may employ a sulfoalkyl ether cyclodextrin solubilizing and complexinig excipient such as CAPTISOL® cyclodextrin (solfobutyl ether (3-cyclodextrin) to form a true aqueous solution and not a suspension. See U.S. Pat. No. 7,034,013, Column 4, line 53 through Column 6, line 22, and Column 6, line 59 through Column 7 line 29, incorporated herein by reference. These types of cyclodextrin formulation minizes the allergic response typically associated with propofol parenteral formulations. See, U.S. Pat. No. 7,034,013 Column 1, beginning line 20 through Column 4, line 11, incorporated herein by reference. This type of formulation also reduces pain on injection as compared to the known emulsion type propofol formulation. A liquid formulation can be lyophilized or otherwise dried to yield a solid formulation.

Tolerance is typically a decrease in drug effect with repeated or chronic dosing. As noted above, in the treatment of chronic pain patients, the pain killer loses its effect and the patient remains in pain despite the administration of the opioid. Indeed, in many instances, narcotics are the most effective treatment for certain conditions. Unfortunately, tolerance to the analgesic effects of narcotics can develop rapidly. Acute tolerance can also be seen during time-limited opioid administration, such as post-operatively or after trauma. The methods of the present invention are useful in preventing tolerance and/or treating the expression of opioid tolerance or related disorders. The present methods provide a very different and unique mechanism of blocking tolerance that has never before been observed with narcotic tolerance.

Also, disclosed herein is a method for treating pain comprising the step of administering to a subject in need thereof a therapeutically effective amount of Gefitinib formulated together with cyclodextrin in an aqueous solution. Opioid analgesics are used to treat pain. However, the long-term use of opioid drugs can produce tolerance to these drugs. An attenuated analgesic effect is a devastating clinical consequence of opioid tolerance as it leads to dose escalation and inadequate pain control. Drug dependence is another devastating side effect of opioids. This occurs due to homeostatic changes after chronic drug administration that results in a withdrawal syndrome when drug administration is stopped. As demonstrated herein, Gefitinib treats, reverses and inhibits development of opioid tolerance and permits morphine to regain effectiveness in situations of neuropathic pain when opioids are normally ineffective. This is also true for GLEEVEC® (imatinib) administration discussed below.

Additionally, disclosed herein is a method for treating pain comprising the step of administering to a subject therapeutically effective amounts of Imatinib as formulated together with cyclodextrin in an aqueous pharmaceutical composition. Opioid analgesics are used to treat pain. However, the long-term use of opioid drugs can produce tolerance to these drugs. An attenuated analgesic effect is a devastating clinical consequence of opioid tolerance as it leads to dose escalation and inadequate pain control, and possibly drug dependence. As demonstrated herein, Imatinib treats, reverses and inhibits the behavioral expression of opioid tolerance and is an effective treatment for pain.

As used herein, the term "therapeutically effective amount" means an amount of a therapeutic agent, or a rate of delivery of a therapeutic agent, effective to facilitate a desired therapeutic effect. The precise desired therapeutic effect (e.g., the degree of pain relief, source of the pain relieved, etc.) will vary according to the condition to be treated, the formulation to be administered, and a variety of other factors that are appreciated by those of ordinary skill in the art. In general, methods of the present disclosure involve the suppression or mitigation of pain in a subject suffering from pain that may be associated with any of a variety of identifiable or unidentifiable etiologies.

Figure 2:
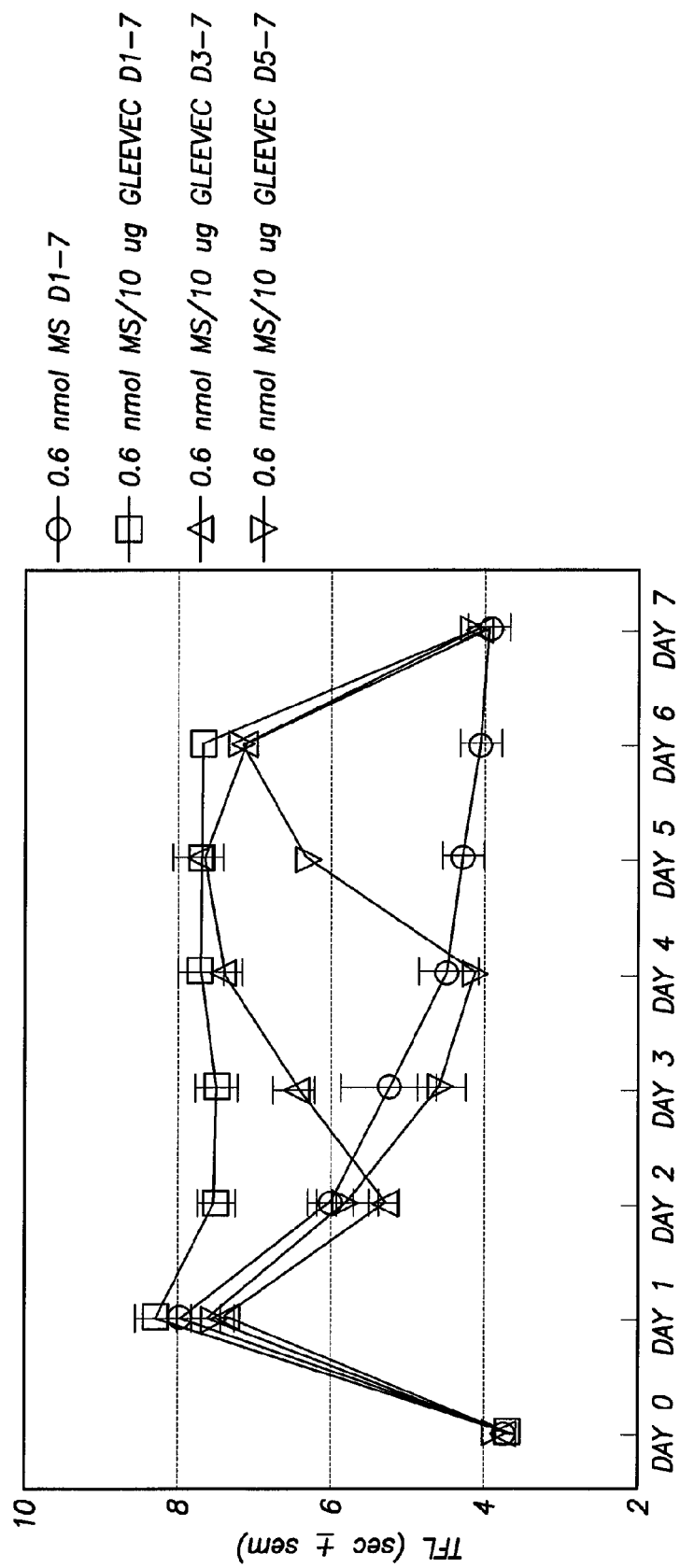
FIG. 2 shows the results of the tail flick latency test demonstrating that GLEEVEC® (imatinib) completely reverses and inhibits the behavioral expression of tolerance.

The behavioral data presented in FIGS. 1 and 2 demonstrate that GLEEVEC® (imatinib) inhibits the behavioral expression, not the development of opioid tolerance. This means when an opioid is administered alone after prolonged treatment with morphine and GLEEVEC® (imatinib), the animals are tolerant. In the case of all other known inhibitors of opioid tolerance, such as NMDA receptor antagonist, the animals are not tolerant. This unique behavioral mechanism shows why PDGF receptor antagonists are uniquely capable of reversing established opioid tolerance.

Figure 3:
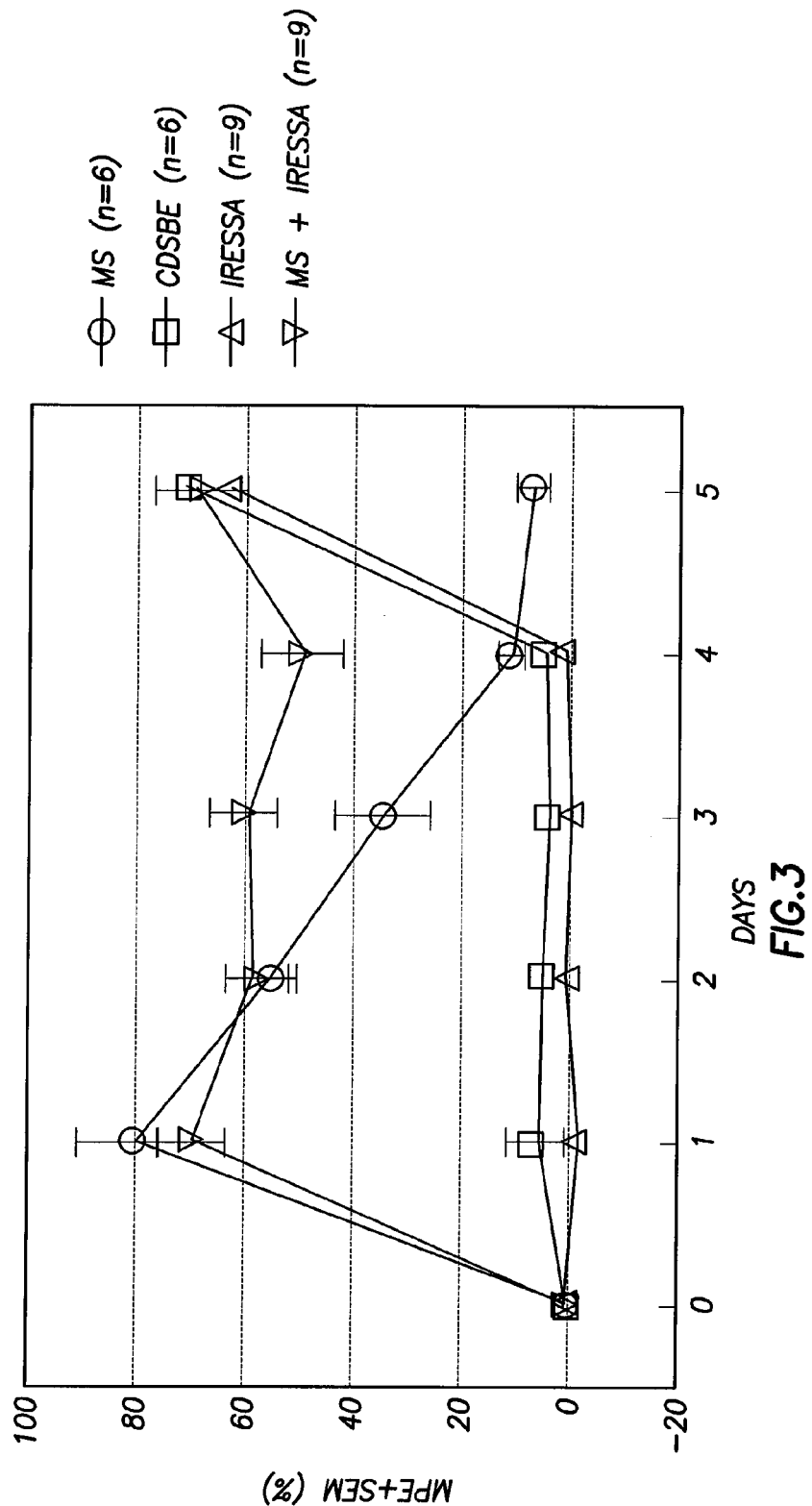
FIG. 3 shows the effectiveness of administering IRESSA® (gefitinib) in 10% CAPTISOL® (sulfobutylether-β-cyclodextrin) in the tail flick latency test, along with controls demonstrating that IRESSA® (gefitinib) and CAPTISOL® (sulfobutylether-β-cyclodextrin) do not exhibit analgesic effects, or interfere with the analgesic effects of morphine administered after chronic GLEEVEC® (imatinib) or CDSBE alone.
Figure 4:
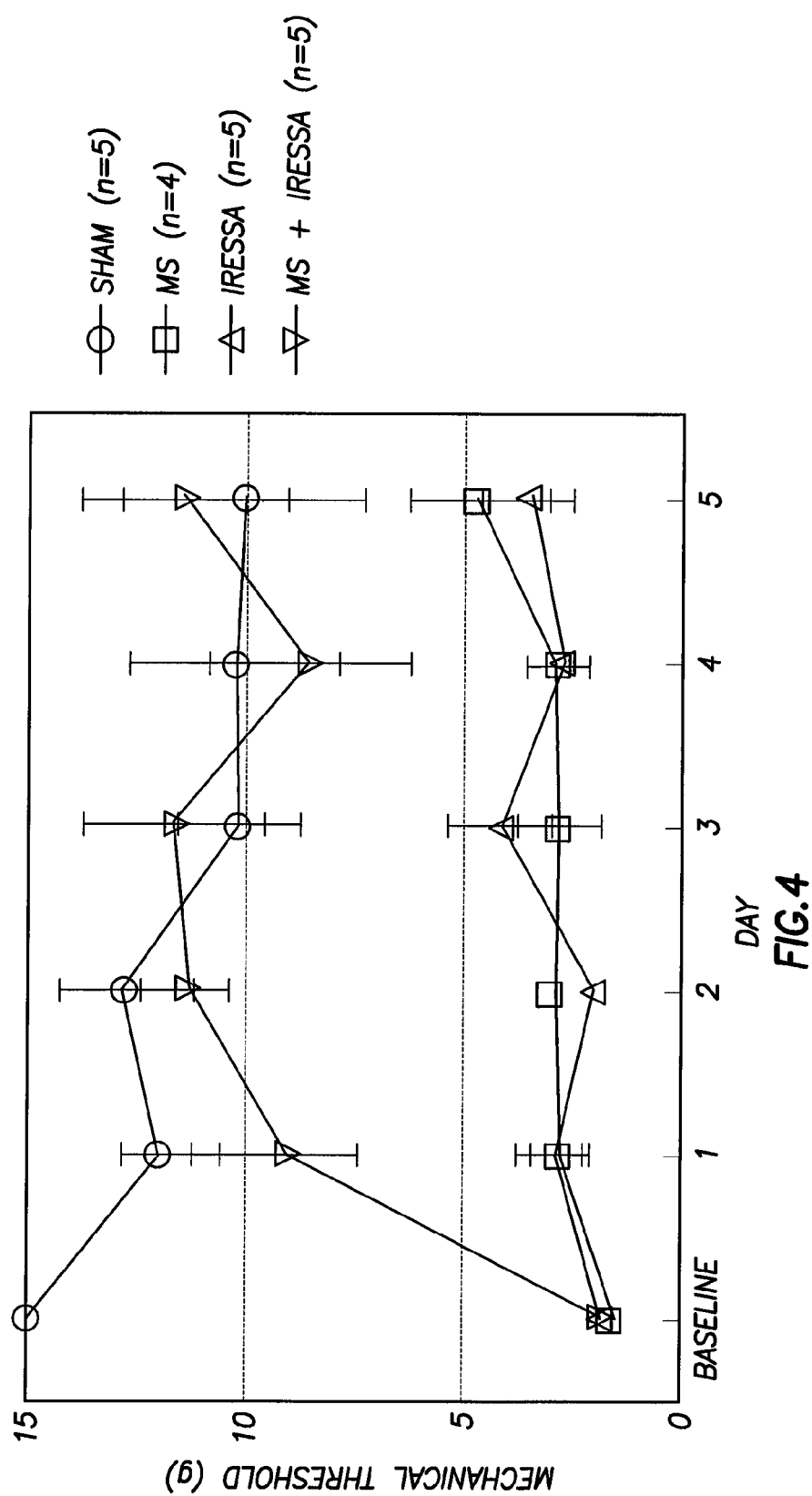
FIG. 4 shows the results of von Frey hair testing in rats that have undergone sciatic nerve ligation, indicating that while neither morphine nor IRESSA® (gefitinib) alone have analgesic properties in this type of pain, the combination of morphine and IRESSA® (gefitinib) provides complete analgesia.

FIGS. 3 and 4 demonstrate the IRESSA® (gefitinib) inhibits the development, not the behavioral expression of opioid tolerance. This means that when opioid is administered alone after prolonged treatment with opioid and IRESSA® (gefitinib), the animals are not tolerant to the effects of opioids.

Figure 5:
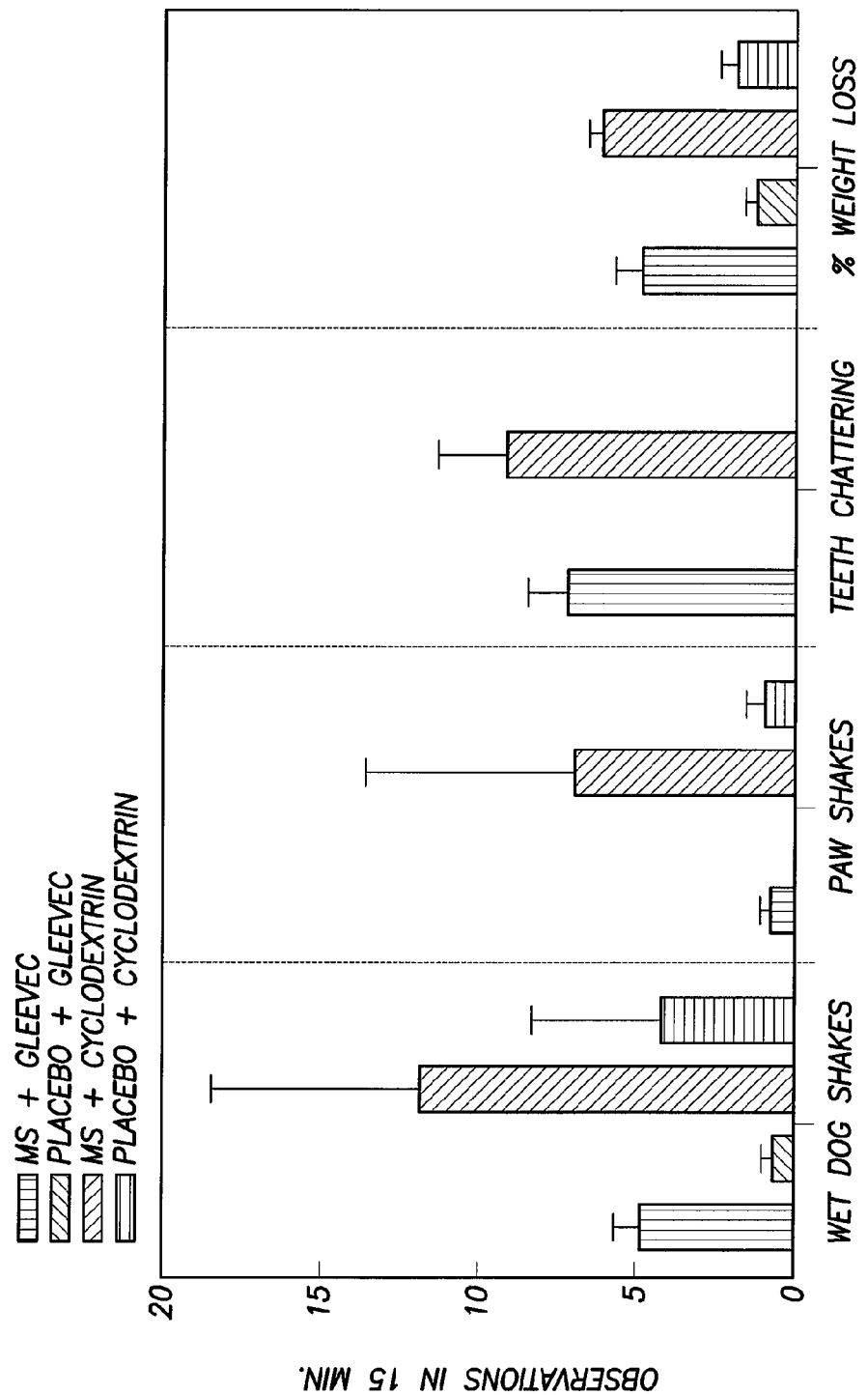
FIG. 5 shows that when animals are made physically dependent upon morphine and subjected to precipitated withdrawal, GLEEVEC® (imatinib) reduces the behavioral expression of paw shakes and wet dog shakes without affecting weight loss, a sign of dependence.

FIG. 5 shows the effect of GLEEVEC® (imatinib) on physical dependence to opioids. Animals were pelleted with continuous release morphine pellets, and treated with GLEEVEC® (imatinib) systemically twice daily. Withdrawal was precipitated by injection of naloxone. Weight loss was not affected by GLEEVEC® (imatinib) administration. However, withdrawal behaviors such as teeth chattering and wet dog shakes were reduced by GLEEVEC® (imatinib) administration. This indicates that GLEEVEC® (imatinib) also inhibits the behavioral expression of drug withdrawal, while the underlying weight loss indicates that the animals were still physically dependent.

Subjects who may benefit from methods and compositions may include individuals suffering from chronic pain due to disease or surgery, have taken or will take an opioid (also known as an opiate) or other analgesic. A subject who experiences or will experience pain, has or is susceptible to having pain sensitivity, neuropathic pain, inflamatory pain, hyperalgesia, allodynia, cancer, diabeties, cardiovascular diseases, multiple sclerosis, HIV-associated neuropathy, diabetic neuropathy, trigeminal neuralgia, postherpetic neuralgia (shingles), phantom limb pain, nerve injury due to trauma or surgery, causalgia, reflex sympathetic dystrophy, complex regional pain syndrome, lower back pain, osteoarthritic pain, pain secondary to inflammatory disease, headache, fibromyalgia, tempromandibular joint syndrome and/or deafferentation pain may benefit from the methods of treatment described herein.

Such subject is administered a "therapeutically effective amount" of a PDGF receptor tyrosine kinase inhibitor. This means that the subject is given an amount of a PDGF receptor tyrosine kinase inhibitor effective to effect a particular result. The results may include: (1) preventing tolerance to an analgesic; (2) reducing tolerance to an analgesic; (3) reversing tolerance to an analgesic; (4) preventing or reducing physical dependence (addiction) on an analgesic as well as reducing the risk of physical dependence on an analgesic; (5) reducing or inhibiting pain sensitization; (6) permitting opioids to become effective analgesics in situations such as neurophathic pain, where opioids are normally ineffective; (7) reducing or inhibiting hyperalgesia and/or allodynia; (8) preventing or reducing the symptoms of withdrawal from an analgesic; (9) inhibition or reduction in PDGF receptor activity and/or expression levels; and (10) reducing the risk or the behavioral expression of addiction or addictive behaviors.

Such subject is administered a "therapeutically effective amount" of an EGF receptor tyrosine kinase inhibitor. This means that the subject is given an amount of an EGF receptor tyrosine kinase inhibitor effective to effect a particular result. The results may include: (1) preventing tolerance to an analgesic; (2) reducing tolerance to an analgesic; (3) reversing tolerance to an analgesic; (4) preventing or reducing physical dependence (addiction) on an analgesic as well as reducing the risk of physical dependence on an analgesic; (5) reducing or inhibiting pain sensitization; (6) permitting oioids to become effective analgesics in situations such as neurophathic pain, where opioids are normally ineffective; (7) reducing or inhibiting hyperalgesia and/or allodynia; (8) preventing or reducing the symptoms of withdrawal from an analgesic; (9) inhibition or reduction in EGF receptor activityand/or expression levels; and (10) reducing the risk or the behavioral expression of addiction or addictive behaviors.

Example 1

Analgesic effectiveness is typically studied using the tail-flick test, where a hot light is shined on a rat's tail and the time required for the rat to move ("flick") its tail recorded (TFL, or tail flick latency). Initial studies showed that when imatinib was spinally administered it inhibited morphine tolerance.

To determine whether GLEEVEC® (imatinib) blocked the development or expression of tolerance, morphine and GLEEVEC® (imatinib) was co-administered for 4 days, and then on day 5 morphine alone was administered. The tail flick latency returned to baseline, indicating that GLEEVEC® (imatinib) blocked the behavioral expression of morphine tolerance as shown in FIG. 1.

To determine whether IRESSA® (gefitinib) blocked the development or expression of tolerance, morphine and IRESSA® (gefitinib) was co-administered for 4 days, and then on day 5 morphine alone was administered. The tail flick latency remained prolonged, indicating that IRESSA® (gefitinib) inhibited the development of morphine tolerance as shown in FIG. 3.

A drug can inhibit the expression of narcotic tolerance if it is analgesic itself or if previous drug administration alters subsequent narcotic analgesia. To determine whether either of these possibilities were the case, animals were treated animals with either the cyclodextrin-based vehicle used to solubilize GLEEVEC® (imatinib) (10% CDSBE) or GLEEVEC® (imatinib) in vehicle for 4 days, and then on the fifth day were given morphine alone. It was found that neither GLEEVEC® (imatinib) nor vehicle was analgesic when administered alone, and they did not alter the analgesic effect of morphine given subsequently on day 5. These data confirm that GLEEVEC® (imatinib) actually inhibits the behavioral expression of morphine tolerance. See FIG. 1.

A drug can inhibit the expression of narcotic tolerance if it is analgesic itself or if previous drug administration altered narcotic analgesia. To determine whether either of these possibilities were the case, animals were treated animals with either the cyclodextrin-based vehicle used to solubilize IRESSA® (gefitinib) (10% CAPTISOL® (sulfobutylether-β-cyclodextrin)) or IRESSA® (gefitinib) in vehicle for 4 days, and then on the fifth day were given morphine alone. It was found that neither IRESSA® (gefitinib) nor vehicle was analgesic when administered alone, and they did not alter the analgesic effect of morphine given on day 5. These data confirm that IRESSA® (gefitinib) actually inhibits the development of morphine tolerance. See FIG. 3.

Figure 9:
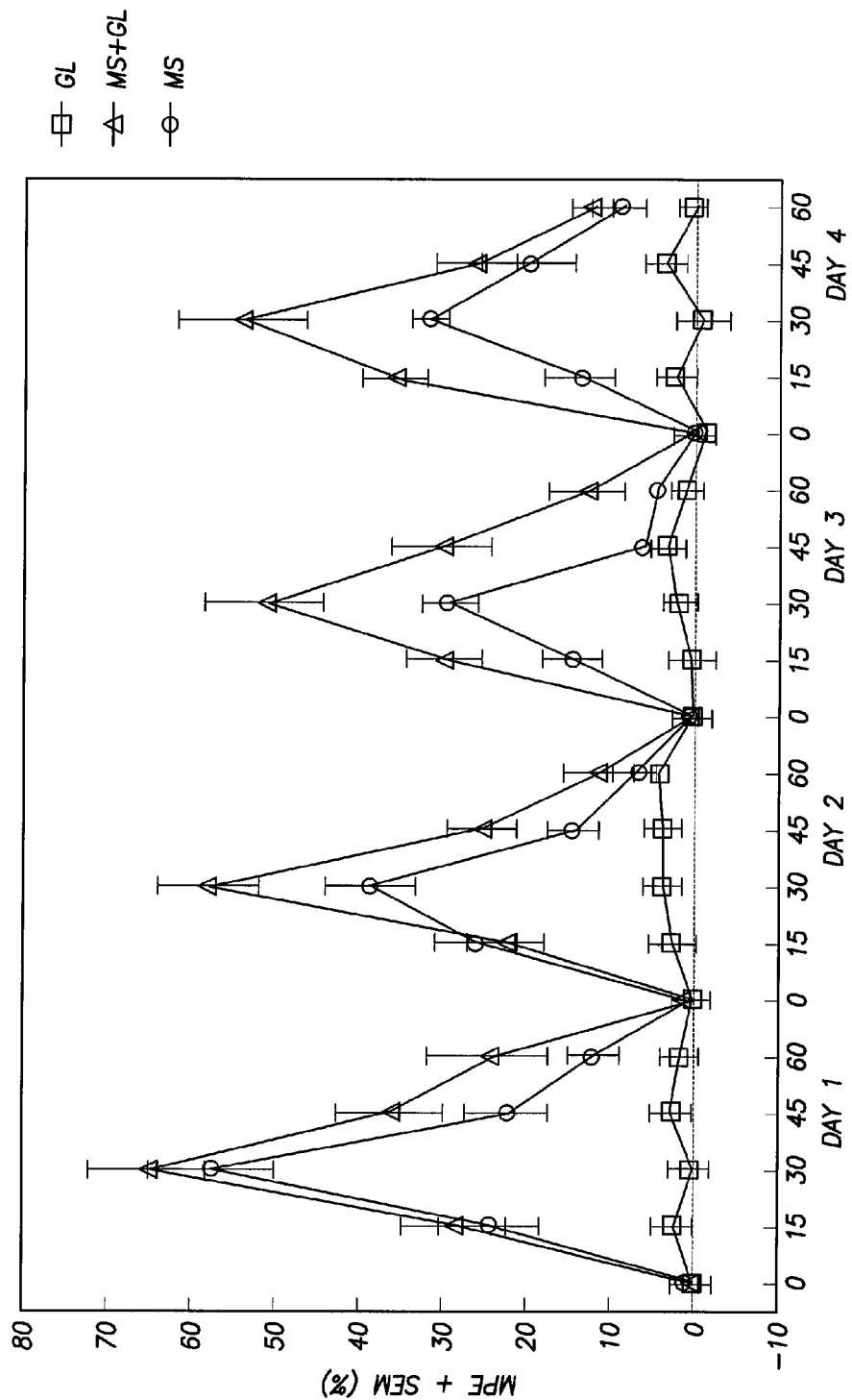
FIG. 9 is a comparison of the time course of morphine analgesia to that of morphine and GLEEVEC® (imatinib) for 4 consecutive days.

Another possible explanation for apparent inhibition of opioid tolerance would be that GLEEVEC® (imatinib) or IRESSA® (gefitinib) could alter morphine pharmacokinetics, causing a different time course of analgesia with co-administration. FIG. 9 compares the time course of morphine analgesia to that of morphine and GLEEVEC® (imatinib) for 4 consecutive days. It is also shown that GLEEVEC® (imatinib) alone has no analgesic effect at any time point. The time course of the analgesic effect does not change—the peak analgesic effect is seen at the 30 minute testing point in both circumstances. This indicates that the increase in analgesia seen when GLEEVEC® (imatinib) is added to morphine is not due to a change in pharmacokinetics, but an inhibition of opioid tolerance. See FIG. 9.

Example 2

Next it was desirable to determine if GLEEVEC® (imatinib) could reverse morphine tolerance. NMDA antagonists, which are known to inhibit the development of morphine tolerance, can only partially reverse morphine tolerance, and cannot reverse established tolerance. In addition, NMDA antagonists are highly toxic (many are chemically related to PCP), which also severely limits their clinical use. To determine whether GLEEVEC® (imatinib) could reverse established morphine tolerance, morphine was given for varying periods of time, and then GLEEVEC® (imatinib) was added. The results are shown in FIG. 2, respectively. As expected, Gleevec inhibited tolerance when co-administered with morphine from the beginning Furthermore, GLEEVEC® (imatinib) completely reversed tolerance at varying points during tolerance development (including completely tolerant animals) after only two days of co-administration with morphine. On day 7, morphine alone was given to all groups. Animals were not analgesic, indicating that GLEEVEC® (imatinib) inhibited the expression of tolerance alone whether it was used to block or reverse this effect. This mechanism of effect has never before been observed.

Example 3

Methods to Test Inhibitors for the Treatment of Chronic Pain

To test the methods of treatment presented herein, we use the sciatic nerve ligation model of Chung et al. (model of neuropathic pain). Chung, J. M., H. K. Kim, and K. Chung, *Segmental Spinal Nerve Ligation Model Of Neuropathic Pain*, Methods Mol Med, 2004. 99: p. 35-45. Animals undergo this ligation procedure, are allowed to recover, and tested for pain sensitivity using Von Frey hairs and/or pressure testing. Animals were administered IRESSA® (gefitinib) to observe if the inhibitors would reduce observed allodynia. IRESSA® (gefitinib) and morphine administered individually had no effect upon allodynia. Remarkably, co-administration of morphine and IRESSA® (gefitinib) provided analgesia after only one administration. See FIG. 4.

Figure 6:
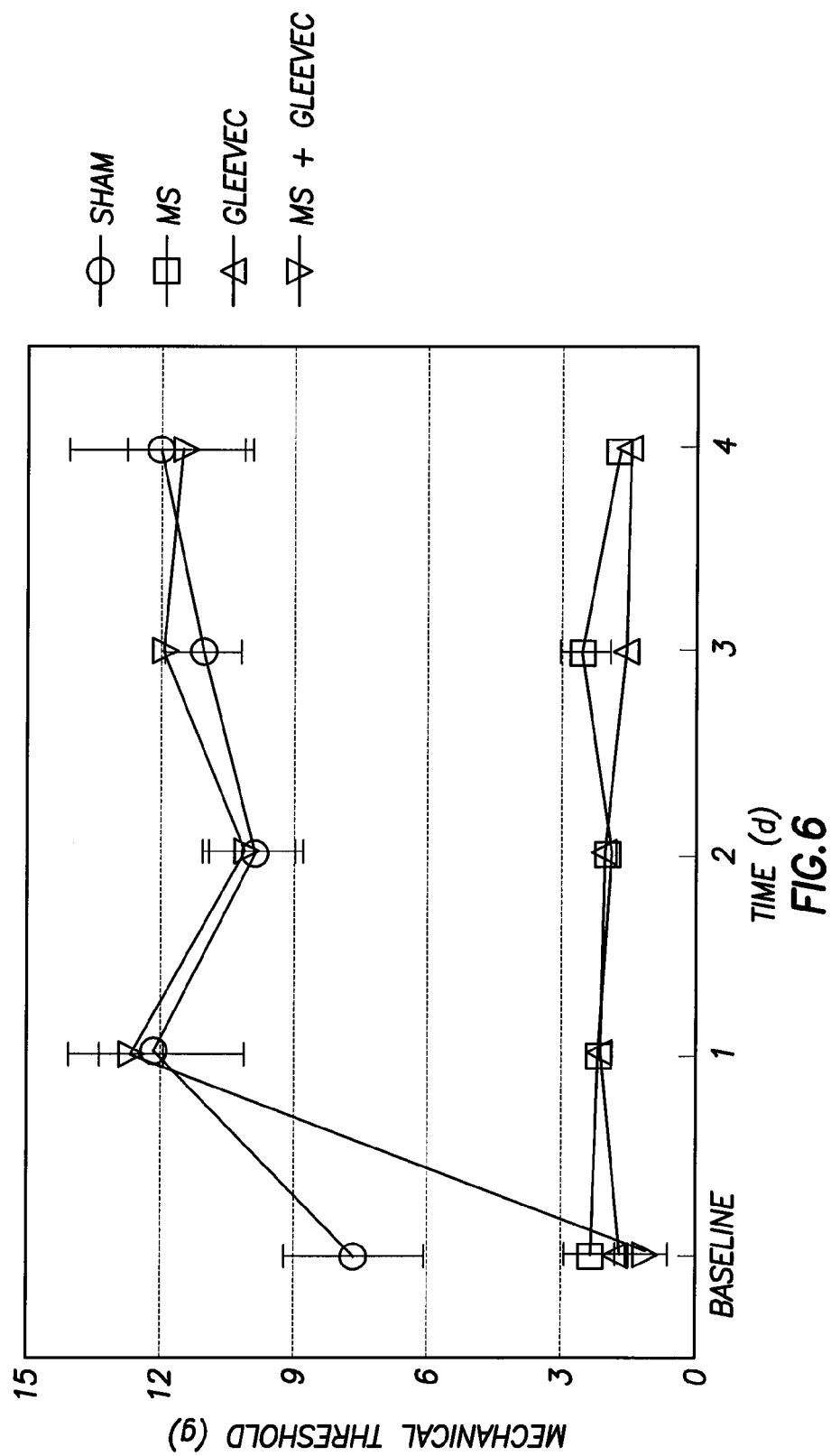
FIG. 6 shows the results of von Frey hair testing in rats that have undergone sciatic nerve ligation, indicating that while neither morphine nor GLEEVEC® (imatinib) alone have analgesic properties in this type of pain, the combination of morphine and GLEEVEC® (imatinib) provides complete analgesia.

To test the methods of treatment presented herein, we use the sciatic nerve ligation model of Chung et al. (model of neuropathic pain). Chung, J. M., H. K. Kim, and K. Chung, *Segmental spinal nerve ligation model of neuropathic pain*. Methods Mol Med, 2004. 99: p. 35-45. Animals undergo this ligation procedure, are allowed to recover, and tested for pain sensitivity using Von Frey hairs and/or pressure testing. Animals were administered GLEEVEC® (imatinib) to observe if the inhibitors would reduce observed allodynia. GLEEVEC® (imatinib) and morphine administered individually had no effect upon allodynia. Remarkably, co-administration of morphine and GLEEVEC® (imatinib) provided analgesia after only one administration. See FIG. 6.

Figure 7:
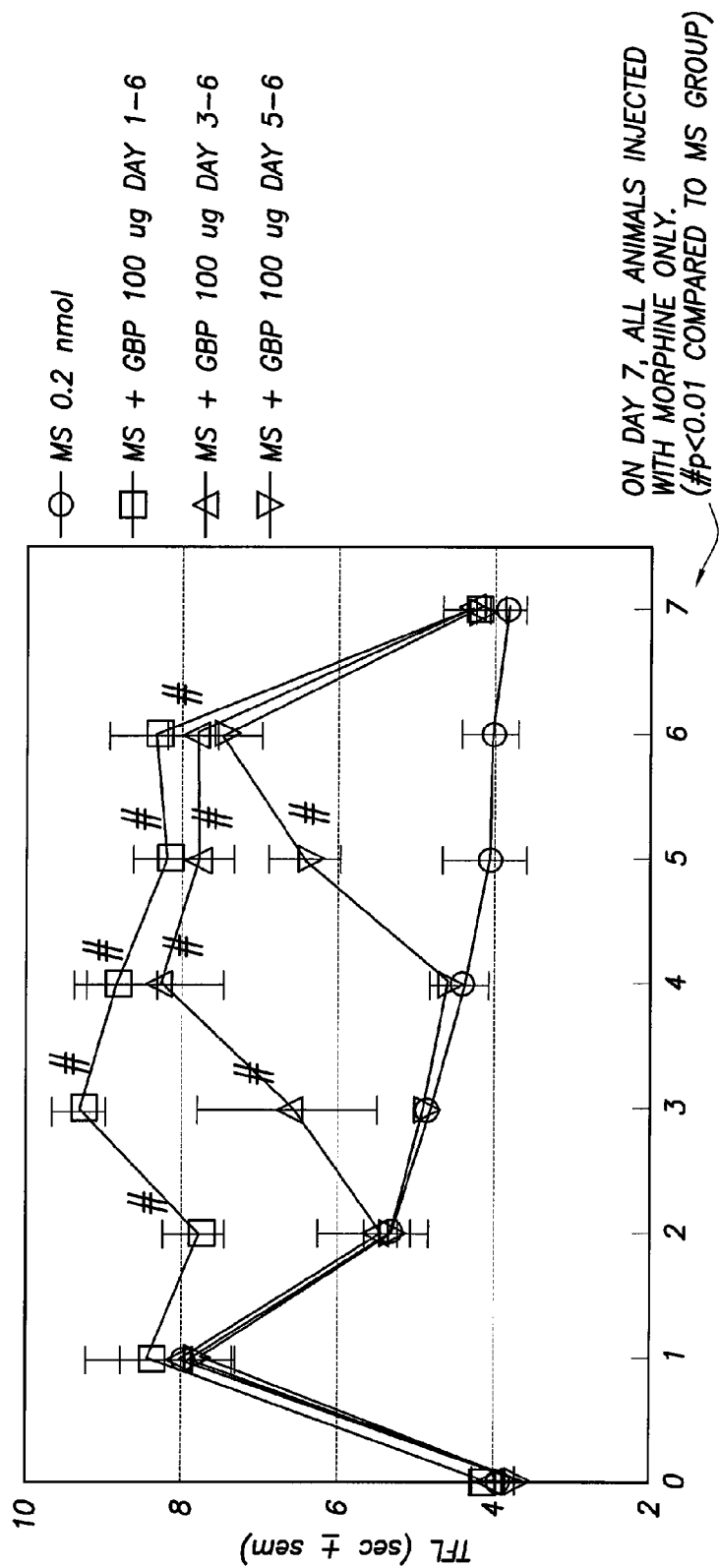
FIG. 7 shows that gabapentin administered with morphine blocks the behavioral expression of tolerance, and reverses established tolerance when infusion is begun at different time points.

As a point of reference, gabapentin, which is often used to treat neuropathic pain, does not cause complete analgesia in this model, either when administered alone or in combination with morphine and also takes several doses to achieve its peak effect. We have also produced data to show that similarly to GLEEVEC® (imatinib), gabapentin blocks the behavioral expression of tolerance, although the doses required are 10 to 100-fold higher. In FIG. 7, we show that Gabapentin administered with morphine blocks tolerance, and reverses established tolerance when infusion is begun at different time points. On the final day of the experiment, when morphine is given alone, the animals were all tolerant. This indicates that gabapentin, like GLEEVEC® (imatinib), blocks the behavioral expression of opioid tolerance. See FIG. 7. Control experiments established that gabapentin was not analgesic itself, nor did it augment morphine's analgesia when administered in combination with morphine.

Figure 8:
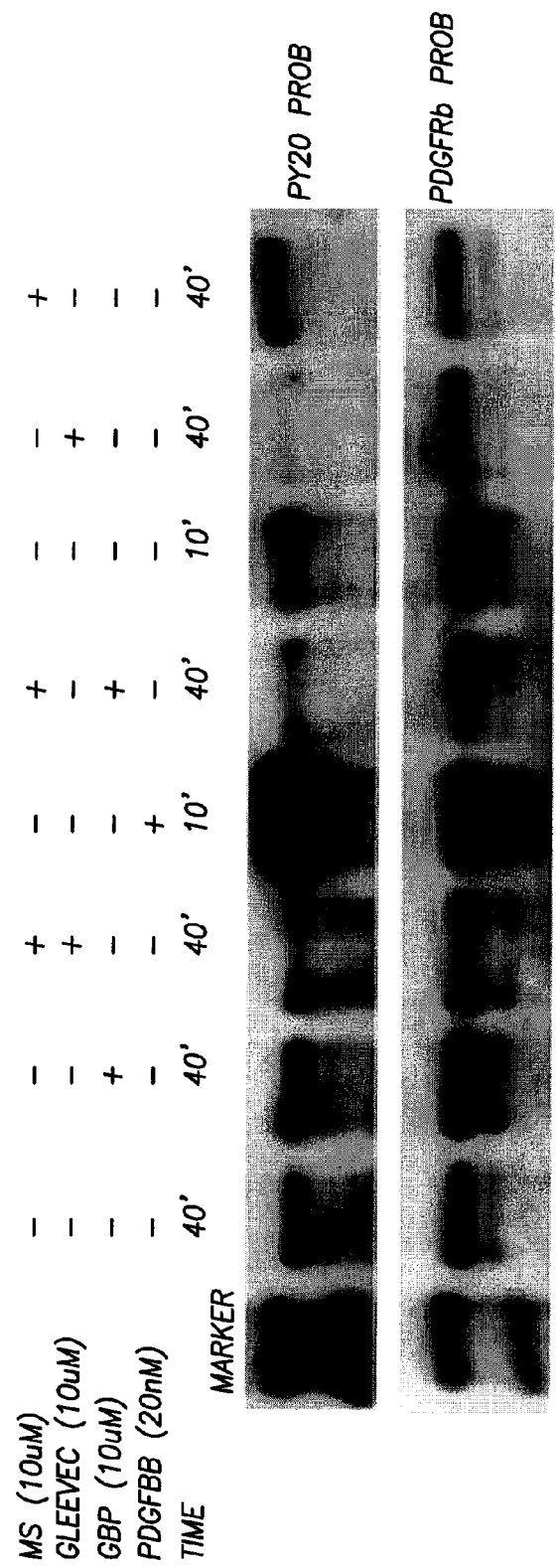
FIG. 8 provides the results of experimentation where morphine caused a 40% increase in PDGFR-beta phosphorylation that was blocked by co-administration of gabapentin.

Studies in cell lines demonstrated that gabapentin blocked PDGFR activation in response to morphine. Cells were treated with morphine, gabapentin, morphine and gabapentin, or water for 40 minutes. Cells were then washed, lysed, and immunoprecipitation was performed using a PDGFR-beta antibody. Western blotting was then performed using PY-20 antibody, which detects tyrosine phosphorylation. Blots were then stripped and re-probed with PDGFR-beta antibody to control for the amount of PDGFR-beta loaded in each lane. These experiments revealed that morphine caused a 40% increase in PDGFR-beta phosphorylation that was blocked by co-administration of gabapentin. See FIG. 8.

Example 4

Treatment of Addiction

PDGFR inhibition may play a prominent role in inhibiting the expression of addictive behavior. Gabapentin has been shown to reduce alcohol intake and self-administration in alcohol dependent animals, as well as reversing anxiogenic effects of alcohol withdrawal in these rats. Roberto, M., et al., *Cellular and Behavioral Interactions of Gabapentin with Alcohol Dependence*. J. Neurosci., 2008. 28(22): p. 5762-5771. These findings indicate that gabapentin alters the behavioral expression of addiction (alcoholism). It is also known that addiction alters dopamine neurotransmission in the mesolimbic dopamine system. Previous investigators have also demonstrated that dopamine receptors can activate PDGFRs to mediate cellular actions. Kotecha, S. A., et al., *A D2 class dopamine receptor transactivates a receptor tyrosine kinase to inhibit NMDA receptor transmission*. Neuron, 2002. 35(6): p. 1111-22.

Therfore, PDGFR inhibition and EGFR inhibition are useful for the treatment of addiction. This could be further tested by administering GLEEVEC® (imatinib) or IRESSA® (gefitinib) systemically using the formulation described above after animals have been made physically dependent ("addicted") to alcohol, cocaine, heroin and other drugs, and express addiction-like behaviors. Animal models to be used are outlined in Roberto, M., et al., *Cellular and Behavioral Interactions of Gabapentin with Alcohol Dependence*. J. Neurosci., 2008. 28(22): p. 5762-5771, Ahmed, S. H. and G. F. Koob, *Transition from Moderate to Excessive Drug Intake: Change in Hedonic Set Point*. Science, 1998. 282((5387) October 9): p. 298-300, and Ahmed, S. H., J. R. Walker, and G. F. Koob, *Persistent increase in the motivation to take heroin in rats with a history of drug escalation*. Neuropsychopharmacology, 2000. 22: p. 413-421. Behaviors to be monitored for alteration include amount of drug self-administration, tests of anxiety, and responses to drug withdrawal. These experiments are currently being undertaken.

I claim:

1. A method of treating morphine tolerance comprising the step of administering to a subject in need thereof a therapeutically effective amount of imatinib administered to the subject in an aqueous pharmaceutical formulation comprising cyclodextrin, cyclodextran, or other cycloamyloses.

2. A method of claim 1 wherein imatinib is administered to the subject in combination with at opioid selected from morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, and ohmefentanyl.

3. The method of claim 1, wherein the drug is administered spinally, intravenously, intraperitoneally, intramuscularly, subcutaneously, or orally.

4. The method of claim 1, wherein the aqueous formulation comprises a cyclodextrin, and the cyclodextrin is cyclodextrin sulfobutyl ether.

5. The method of claim 4, wherein the cyclodextrin sulfobutyl ether is sulfobutylether-7-b-cyclodextrin.

* * * * *

UNITED STATES PATENT AND TRADEMARK OFFICE
CERTIFICATE OF CORRECTION

PATENT NO. : 8,501,740 B2
APPLICATION NO. : 12/682064
DATED : August 6, 2013
INVENTOR(S) : Howard Gutstein Page 1 of 1

It is certified that error appears in the above-identified patent and that said Letters Patent is hereby corrected as shown below:

In the Claims:

In claim 2, column 14, line 32, delete "with at" and insert --with a µ-- therefor.

Signed and Sealed this
Twelfth Day of November, 2013

Teresa Stanek Rea
*Deputy Director of the United States Patent and Trademark Office*